United States Patent [19]

Yuki et al.

[11] Patent Number: 4,728,644
[45] Date of Patent: Mar. 1, 1988

[54] PURINE DERIVATIVE AND PHARMACEUTICAL COMPOSITION

[75] Inventors: Hiroshi Yuki, Toyonaka; Hiroyuki Sueoka, Buzen; Mitsuyoshi Yasumoto, Fukuoka; Michio Terasawa, Nakatsu; Tomonori Imayoshi, Nakatsu, all of Japan

[73] Assignee: Yoshitomi Pharmaceutical Industries, Ltd., Osaka, Japan

[21] Appl. No.: 768,535

[22] PCT Filed: Dec. 28, 1984

[86] PCT No.: PCT/JP84/00633

§ 371 Date: Jul. 22, 1985

§ 102(e) Date: Jul. 22, 1985

[87] PCT Pub. No.: WO85/03077

PCT Pub. Date: Jul. 18, 1985

[30] Foreign Application Priority Data

Jan. 13, 1984 [JP] Japan .................................. 59-4986

[51] Int. Cl.$^4$ .................... C07D 473/04; A61K 31/52
[52] U.S. Cl. .................................. 514/212; 514/227; 514/254; 514/261; 544/61; 544/118; 544/276; 544/277
[58] Field of Search ................. 544/277, 276, 61, 118; 514/261, 254, 222, 227

[56] References Cited

U.S. PATENT DOCUMENTS 4,473,571 9/1984 Lesher et al. ...................... 544/277

FOREIGN PATENT DOCUMENTS 1201997 8/1974 United Kingdom .

Primary Examiner—Nicholas S. Rizzo
Attorney, Agent, or Firm—Wenderoth, Lind & Ponack

[57] ABSTRACT

Purine derivatives of the formula:

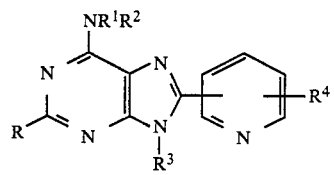

wherein R is hydrogen, alkyl or phenyl which may be substituted by at least one halogen, lower alkyl or lower alkoxy; each of $R^1$ and $R^2$ is hydrogen, alkyl, cycloalkyl, hydroxyalkyl, dialkylaminoalkyl, cyclic aminoalkyl, alkenyl or aralkyl, or $R^1$ and $R^2$ together with the adjacent nitrogen atom form a heterocycle; and each of $R^3$ and $R^4$ is hydrogen or lower alkyl, and pharmaceutically acceptable acid addition salts thereof and/or hydrates, methods of preparing said compounds and pharmaceutical compositions containing said compounds. The purine compounds exhibit antiinflammatory, analgesic, antipyretic and antiallergic activity, and inhibitory activity on platelet aggregation, and are useful as drugs.

9 Claims, No Drawings

PURINE DERIVATIVE AND PHARMACEUTICAL COMPOSITION

FIELD OF THE INVENTION

The present invention relates to novel and pharmaceutically useful purine derivatives.

BACKGROUND OF THE INVENTION

Anti-tumor active 8-(2-, 3-, and 4-pyridyl)purine compounds are disclosed in British Pat. No. 1201997, 8-phenyladenine compounds exhibiting xanthineoxydase inhibitory activity are disclosed in Journal of Medicinal Chemistry, vol. 11, p. 656, 1968, and 9-purinyl hydroxy alkanoic acid derivatives useful as hypocholesterolaemic agents are disclosed in Belgium Pat. No. 737949.

However, there are no disclosures on purine derivatives having antiinflammatory, analgesic, antipyretic or antiallergic activity, or inhibitory activity on platelet aggregation, in the prior art, including the above documents.

Therefore, the purpose of the present invention is to provide novel purine derivatives having antiinflammatory, analgesic, antiseptic and antiallergic activity, and inhibitory activity on platelet aggregation.

As a result of intensive investigations, the present inventors have completed the present invention.

The present invention relates to purine derivatives of the formula:

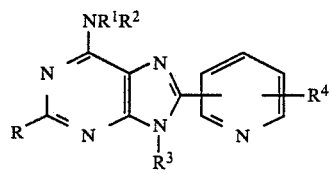

(I)

or pharmaceutically acceptable acid addition salts thereof and/or hydrates thereof.

In the above formula (I), R is a hydrogen atom, an alkyl group or a phenyl group which may be optionally substituted by at least one substituent selected from a halogen atom, a lower alkyl group and a lower alkoxy group; each of $R^1$ and $R^2$ is a hydrogen atom, an alkyl group, a cycloalkyl group, a hydroxyalkyl group, a dialkylaminoalkyl group, a cyclic amino alkyl group, an alkenyl group or an aralkyl group, or $R^1$ and $R^2$ together with the adjacent nitrogen atom form a heterocycle; and each of $R^3$ and $R^4$ is a hydrogen atom or a lower alkyl group.

In this specification, the alkyl group means a straight or branched alkyl group having 1 to 8 carbon atoms and includes, for example, methyl, ethyl, propyl, isopropyl, butyl, isobutyl, tert-butyl, pentyl, hexyl and octyl; the halogen atom means fluorine, chlorine, bromine and iodine. The lower alkyl group means a straight or branched alkyl group having 1 to 4 carbon atoms and includes, for example, methyl, ethyl, propyl, isopropyl, butyl, isobutyl and tert-butyl. The lower alkoxy group means a straight or branched alkoxy group having 1 to 4 carbon atoms and includes, for example, methoxy, ethoxy, propoxy, isopropoxy, butoxy and tert-butoxy. The cycloalkyl group means a cyclic saturated hydrocarbon group having 3 to 7 carbon atoms and includes cyclopropyl, cyclobutyl, cylopentyl, cyclohexyl and cycloheptyl. The hydroxyalkyl group has 1 to 8 carbon atoms in the alkyl moiety and includes, for example, 2-hydroxyethyl, 2-hydroxypropyl, 3-hydroxypropyl and 4-hydroxybutyl. The dialkylaminoalkyl group has 1 to 8 carbon atoms in each alkyl moiety and includes, for example, 2-dimethylaminoethyl, 2-diethylaminoethyl, 3-dimethylaminopropyl and 4-dimethylaminobutyl. The cyclic aminoalkyl group may have at least one nitrogen atom, which may be substituted by a lower alkyl group or a hydroxyalkyl group, oxygen atom or sulfur atom as other heteroatom in the cyclic amino moiety and has 1 to 8 carbon atoms in the alkyl moiety, and includes, for example, 1-pyrrolidinylmethyl, 2-(1-pyrrolidinyl)ethyl, 2-piperidinoethyl, 2-morpholinoethyl, 3-thiomorpholinopropyl, 2-(1-piperazinyl)ethyl, 2-(4-methyl-1-piperazinyl)ethyl, 2-[4-(2-hydroxyethyl)-1-piperazinyl]ethyl and 2-(4-methyl-1-homopiperazinyl)ethyl. The alkenyl group means a straight or branched alkenyl group having 2 to 8 carbon atoms and includes, for example, vinyl, allyl, isopropenyl, butenyl, pentenyl, 1-methyl-3-butenyl and hexenyl. The aralkyl group means an arylalkyl group and includes, for example, benzyl, 2-phenylethyl and 3-phenylpropyl. The heterocyle formed by $R^1$ and $R^2$ together with the adjacent nitrogen atom may have at least one nitrogen atom, which may be substituted by a lower alkyl group or a hydroxyalkyl group, oxygen atom or sulfur atom as other heteroatom, and includes, for example, 1-pyrrolidinyl, piperidino, 1-piperazinyl, 4-methyl-1-piperazinyl, 4-(2-hydroxyethyl)-1-piperazinyl, 1-homopiperazinyl, 4-methyl-1-homopiperazinyl, morpholino and thiomorpholino.

The compounds of formula (I) of the present invention can, for example, be prepared according to the following methods: (1) A method which comprises reacting a compound of the formula:

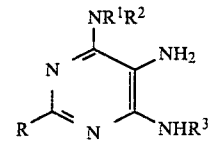

(II)

wherein each symbol is as defined above, with a compound of the formula:

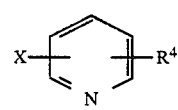

(III)

wherein X is a carboxyl group, a lower alkoxycarbonyl group, a cyano group, a haloformyl group or a thioamide group and $R^4$ is as defined above.

The reaction is suitably performed in accordance with the kinds of substituent X of the compounds of formula (III), and is preferably carried out at 0°–250° C. in the presence of a condensation agent such as polyphosphoric acid, polyphosphate ester, phosphorus oxychloride, p-toluenesulfonic acid, hydrochloric acid, hydrobromic acid, phosphoric acid, thionyl chloride, phosphorus pentoxide, sodium ethoxide or potassium tert-butoxide, and if necessary, in an inert solvent such as benzene, toluene, xylene, pyridine, ethanol, isopropanol, ethylene glycol, diethylene glycol dimethyl ether, dimethylformamide or dioxane. (2) A method which comprises reacting a compound of the formula:

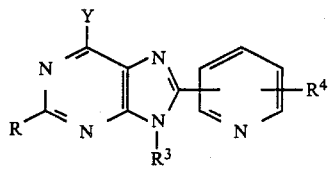

wherein Y is a halogen atom or a lower alkylthio group such as methylthio or ethylthio and the other symbols are as defined above, with a compound of the formula:

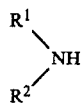

wherein each symbol is as defined above.

The reaction is carried out at 50°–250° C. under refluxing or in a pressure vessel without solvent or preferably in an inert solvent such as water, toluene, xylene, pyridine, ethanol, isopropanol or dimethylformamide.

The purine derivatives of formula (I) according to the present invention can be provided as a medicine in the form of a free base, an acid addition salt thereof or a hydrate thereof.

A pharmaceutically acceptable acid addition salt thereof can be used as the acid addition salt, and includes, for example, salts of inorganic and organic acids such as hydrochloric, sulfuric, hydrobromic, phosphoric, formic, acetic, oxalic, fumaric, maleic, citric, tartaric, malic, mandelic, methanesulfonic and toluenesulfonic acids.

The compounds of formula (I), the acid addition salts thereof and hydrates thereof exhibit antiinflammatory, analgesic and antipyretic activities, for example, according to the carrageenan foot edema method of Winter et al., phenylquinone writhing method of Hendershot et al. or in guinea pigs having a fever caused by lipopolysaccharide (LPS) according to Kobayashi et al.

Ulcer-inducing effects are not observed in the compounds of the present invention, unlike the acid and nonsteroid antiinflammatory agents such as aspirin, and the compounds of the present invention are useful antiinflammatory agents, analgesics and antipyretics having less side effects.

The compounds of the present invention also inhibit rat adjuvant arthritis of Newbold et al., and are useful in the treatment of rheumatoid arthritis or osteoarthritis.

Further, the compounds of the present invention inhibit the reverse passive arthus reaction according to the method of Plam et al., and are useful in the treatment of various diseases caused by Type III allergic reaction such as rheumatoid arthritis, systemic erythematodes, serum sickness, hypersensitivity pneumonitis or chronic glomeruler nephritis. Furthermore, the compounds of the present invention inhibit the production of SRS-A which is accompanied with phagocytosis of Bordetella pertussis by rat celiac leukocyte according to the partly modified method of D. Rosa et al., and are useful as drugs for the treatment of bronchial asthma. In addition, the compounds of the present invention are useful as improving agents for improving the circulatory function.

The compounds of the present invention can be administered orally or parenterally. In oral administration, the compounds are mixed with a conventional and pharmaceutically acceptable additive such as a carrier, an excipient or a diluent to form powder, tablets, capsules, troches, solutions, syrup and granules. In parenteral administration, the compounds can be used as injectable solution for intravenous, intramuscular or subcutaneous injections, suppositories or cream ointments in the form of solutions or non-aqueous suspensions.

The single dose may vary depending on the patient's symptoms, body weight or age and so on, but preferably ranges from 0.1 to 10 mg per kg depending on body weight for human adults.

The following examples explain the present invention in more detail, but they are not to be construed as limiting the present invention.

EXAMPLE 1

A mixture obtained by grinding homogeneously 5 g of 4,5-diamino-6-diethylaminopyrimidine and 3.4 g of isonicotinic acid in a mortar is added to 110 ml of phosphorus oxychloride under stirring, and refluxed with heating for 3 hours. The reaction solution is concentrated and 180 ml of water is added to the residual oil. The resulting solution is neutralized with an ammonia solution and the precipitated crystals are filtered and washed with water. Recrystallization from ethanol gives 3.4 g of 6-diethylamino-8-(4-pyridyl)purine, melting at 260°–262° C.

EXAMPLE 2

A mixture of 3 g of 4,5-diamino-6-(4-methyl-1-piperazinyl) pyrimidine, 1.8 g of isonicotinic acid and 45 g of polyphosphoric acid is stirred at 160°–170° C. for 4 hours under nitrogen atmosphere. To the resultant mixture is added 200 ml of water and the solution is neutralized with an ammonia solution. The crystals precipitated are filtered and washed with water, and then recrystallized from methanol to give 1.5 g of 6-(4- methyl-1-piperazinyl)-8-(4-pyridyl)purine, melting at 333°–335° C.

EXAMPLE 3

A homogeneous mixture obtained by grinding 5 g of 4,5-diamino-6-diethylamino-2-methylpyrimidine and 3.4 g of isonicotinic acid in a mortar is added to 110 ml of phosphorus oxychloride under stirring, and refluxed with heating for 3 hours. The reaction solution is concentrated and 180 ml of water is added to the residual oil. The aqueous solution is neutralized with an ammonia solution and the crystals precipitated are filtered and purified by column chromatography on silica gel with a mixture of chloroform and methanol (10:1) as an eluent. Recrystallization from methanol gives 2.3 g of 6-diethylamino-2-methyl-8-(4-pyridyl)purine, melting at 228°–230° C.

EXAMPLE 4

To 80 ml of phosphorus oxychloride are added 4 g of 4,5-diamino-6-(4-methyl-1-piperazinyl)-2-phenylpyrimidine and 1.7 g of isonicotinic acid, and the mixture is refluxed with heating for 6 hours under stirring. The reaction solution is concentrated and 700 ml of water is added to the residual oil. The solution is neutralized with an ammonia solution and the crystals precipitated are filtered, and then washed with water. Recrystallization from a mixture of chloroform and methanol (2:1)

gives 2.7 g of 6-(4-methyl-1-piperazinyl)-2-phenyl-8-(4-pyridyl)purine, melting at 333°–337° C.

EXAMPLE 5

A mixture of 6 g of 6-methylthio-8-(4-pyridyl)purine, 30 ml of an aqueous solution of 70% ethylamine and 30 ml of water is stirred at 150° C. for 10 hours in an autoclave. The reaction mixture is concentrated and the residual oil is dissolved into methanol. To the solution is added about 3 g of activated charcoal. The mixture is shaken well, filtered and then concentrated. The resulting crystals are recrystallized from a 1:1 mixture of ethanol and water to give 1.7 g of 6-ethylamino-8-(4-pyridyl)purine, melting at 308°–310° C. The following compounds can also be prepared in a similar manner as the above examples and according to the methods described in the specification:

6-Dimethylamino-8-(3-pyridyl)purine, melting at 325°–326° C.

6-Dimethylamino-8-(4-pyridyl)purine, melting at 335°–336° C.

6-Diethylamino-8-(2-pyridyl)purine, melting at 239°–241° C.

6-Diethylamino-8-(3-pyridyl)purine, melting at 260°–262° C.

6-Diisopropylamino-2-methyl-8-(4-pyridyl)purine, melting at 213°–215° C.

6-Diisopropylamino-2-methyl-8-(3-pyridyl)purine, melting at 234°–236° C.

6-Morpholino-8-(4-pyridyl)purine, melting at 358°–360° C.

2-Methyl-6-morpholino-8-(3-pyridyl)purine, melting at 306°–307° C.

2-Methyl-6-morpholino-8-(4-pyridyl)purine, melting at 311°–313° C.

6-Amino-9-ethyl-2-methyl-8-(2-pyridyl)purine, melting at 243°–245° C.

2-Methyl-6-piperidino-8-(3-pyridyl)purine, melting at 293°–295° C.

2-Methyl-6-piperidino-8-(4-pyridyl)purine, melting at 273°–279° C.

8-(4-Pyridyl)-6-(1-pyrrolidinyl)purine, melting at 345°–350° C.

8-(3-Pyridyl)-6-(1-pyrrolidinyl)purine, melting at 324°–325° C.

2-Methyl-8-(4-pyridyl)-6-(1-pyrrolidinyl)purine, melting at 304°–305° C.

6-Diethylamino-2,9-dimethyl-8-(4-pyridyl)purine, melting at 130°–131° C.

2,9-Dimethyl-6-piperidino-8-(4-pyridyl)purine, melting at 151°–153° C.

6-Diethylamino-9-methyl-8-(4-pyridyl)purine, melting at 109°–110° C.

6-Diethylamino-2-phenyl-8-(4-pyridyl)purine, melting at 314°–316° C.

2-Phenyl-6-piperidino-8-(4-pyridyl)purine, melting at above 360° C.

2-Phenyl-8-(4-pyridyl)-6-(1-pyrrolidinyl)purine, melting at above 360° C.

2-(4-Methylphenyl)-6-morpholino-8-(3-pyridyl)purine, melting at 318°–320° C.

2-(4-Fluorophenyl)-6-piperidino-8-(4-pyridyl)purine, melting at above 360° C.

2-(4-Fluorophenyl)-8-(4-pyridyl)-6-(1-pyrrolidinyl)purine, melting at above 350° C.

6-[N-Methyl-N-(2-dimethylaminoethyl)amino]-8-(4-pyridyl)purine, melting at 221°–223° C.

6-Dibutylamino-8-(4-pyridyl)purine, melting at 236°–237° C.

6-Diethylamino-2-(4-methoxyphenyl)-8-(4-phenyl)purine, melting at 250°–252° C.

2-Methyl-6-(4-methyl-1-piperazinyl)-8-(4-pyridyl)purine, melting at 276°–278° C. with decomposition 6-(4-Methyl-1-piperazinyl)-2-(4-methylphenyl)-8-(4-pyridyl)purine, melting at 301°–305° C. with decomposition 6-[N-(2-Hydroxyethyl)-N-methylamino]-8-(4-pyridyl)purine, melting at 286°–289° C.

6-Cyclohexylamino-8-(4-pyridyl)purine, melting at 317°–319° C.

6-(2-Phenylethyl)amino-8-(4-pyridyl)purine, melting at 290°–292° C.

2-(4-Fluorophenyl)-6-(4-methyl-1piperazinyl)-8-(4-pyridyl)purine, melting at 320°–330° C. with decomposition 6-[4-(2-Hydroxyethyl)-1-piperazinyl]-8-(4-pyridyl)purine, melting at 302°–306° C.

6-(2-Morpholinoethylamino)-8-(4-pyridyl)purine, melting at 268°–271° C.

2-(3,4-Dimethoxyphenyl)-6-(4-methyl-1piperazinyl)-8-(4-pyridyl) purine, melting at 281°–283° C.

6-(4-Methyl-1homopiperazinyl)-2-phenyl-8-(4-pyridyl)purine, melting at 318°–321° C.

6-[N,N-Bis(2-hydroxyethyl)amino]-8-(4-pyridyl)purine, melting at 243°–248° C.

6-Octylamino-8-(4-pyridyl)purine, melting at 245°–246° C.

2-Isopropyl-8-(4-pyridyl)-6-(1-pyrrolidinyl)purine, melting at 305°–307° C.

2-Isopropyl-6-(4-methyl-1-piperazinyl)-8-(4-pyridyl)purine, melting at 271°–273° C.

2-(4-Chlorophenyl)-6-(4-methyl-1-piperazinyl)-8-(4-pyridyl)purine melting at 306°–310° C.

2-Methyl-6-piperidino-8-(5-ethyl-2-pyridyl)purine, melting at 196°–198° C.

6-[4-(2-Hydroxyethyl)-1-piperazinyl]-2-phenyl-8-(4-pyridyl)purine, melting at 324°–326° C.

6-[N-(3-Dimethylaminopropyl)-N-methylamino]-2-phenyl-8-(4-pyridyl)purine, melting at 278°–281° C.

6-[(1-Methyl-3-butene-1-yl)amino]-8-(4-pyridyl)purine, melting at 290°–293° C.

Formulation Example

Tablets containing 50.0 mg of Compound (I) can be prepared in accordance with the following compositions:

| Compound (I) | 50.0 mg |
| Lactose | 68.5 mg |
| Corn starch | 30.0 mg |
| Crystalline cellulose | 20.0 mg |
| Polyvinyl Pyrrolidone K-30 | 2.0 mg |
| Talc | 4.0 mg |
| Magnesium stearate | 0.5 mg |
| | 175.0 mg |

Compound (I) is crushed with an atomizer to make a fine powder having an average particle size below 10μ. The fine powder of Compound (I), lactose, corn starch and crystalline cellulose are mixed well in a kneader and then kneaded with a binder prepared from polyvinyl pyrrolidone. The wet mass is passed through a 200 mesh sieve and then dried in an oven at 50° C. The dry granulate containing 3–4% of water content is forced through a 24 mesh sieve. Talc and magnesium stearate are mixed

What is claimed is:

1. A purine derivative of the formula:

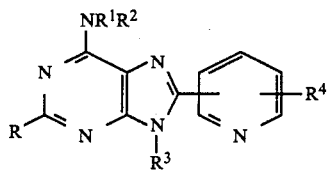

wherein R is a hydrogen atom, $C_{1-8}$ alkyl group or a phenyl group which may be substituted by at least one substituent selected from a halogen atom, a $C_{1-4}$ alkyl group and a $C_{1-4}$ alkoxy group; each of $R^1$ and $R^2$ is a hydrogen atom, a $C_{1-8}$ alkyl group, a $C_{3-7}$ cycloalkyl group, a hydroxy-$C_{1-8}$ alkyl group, a di-$C_{1-8}$ alkylamino-$C_{1-8}$ alkyl group, a cyclic amino-$C_{1-8}$ alkyl group wherein the cyclic amino is selected from 1-pyrrolidinyl, piperidino, morpholino, thiomorpholino, 1-piperazinyl, 4-methyl-1-piperaznyl, 4-(2-hydroxyethyl)-1-piperazinyl and 4-methyl-1-homopiperazinyl, a $C_{2-8}$ alkenyl group or a phenyl-$C_{1-3}$ alkyl group, or $R^1$ and $R^2$ together with the adjacent nitrogen atom form a heterocycle selected from 1-pyrrolidinyl, piperidino, 1-piperazinyl, 4-methyl-1-piperazinyl, 4-(2-hydroxyethyl)-1- piperazinyl, 1-homopiperazinyl, 4-methyl-1-homopiperazinyl, morpholino and thiomorpholino, and each of $R^3$ and $R^4$ is a hydrogen atom or a $C_{1-4}$ alkyl group, or
  a pharmaceutically acceptable acid addition salt thereof.

2. The compound of claim 1, namely 2-methyl-8-(4-pyridyl)-6-(1-pyrrolidinyl)purine.

3. The compound of claim 1, namely 2-methyl-6-piperidino-8-(4-pyridyl)purine.

4. The compound of claim 1, namely 6-diethylamino-2-methyl-8-(4-pyridyl)purine.

5. The compound of claim 1, namely 2-methyl-6-morpholino-8-(4-pyridyl)purine.

6. The compound of claim 1, namely 2-isopropyl-8-(4-pyridyl)-6-(1-pyrrolidinyl)purine.

7. The compound of claim 1, namely 6-(4-methyl-1-piperazinyl)-2-phenyl-8-(4-pyridyl)purine.

8. The compound of claim 1, namely 6-diethylamino-8-(4-pyridyl)purine.

9. A pharmaceutical composition for exhibiting antiinflammatroy, analgesic, antipyretic or antiallergic activity or inhibitory activity on platelet aggregation, comprising a therapeutically effective amount of the compound of claim 1 and a pharmaceutically acceptable additive.

* * * * *